(12) United States Patent
Lukac et al.

(10) Patent No.: US 8,011,923 B2
(45) Date of Patent: Sep. 6, 2011

(54) METHOD FOR OPERATING A LASER SYSTEM FOR BLEACHING TEETH

(75) Inventors: Matjaz Lukac, Ljubljana (SI); Boris Cencic, Ljubljana (SI)

(73) Assignee: Fotona d.d., Ljubljana (SI)

( * ) Notice: Subject to any disclaimer, the term of this patent is extended or adjusted under 35 U.S.C. 154(b) by 297 days.

(21) Appl. No.: 12/202,345

(22) Filed: Sep. 1, 2008

(65) Prior Publication Data

US 2009/0061391 A1   Mar. 5, 2009

(30) Foreign Application Priority Data

Sep. 1, 2007 (EP) .................................. 07017169
Aug. 7, 2008 (EP) .................................. 08014107

(51) Int. Cl.
*A61C 1/00* (2006.01)
*A61C 5/00* (2006.01)

(52) U.S. Cl. ......................................... 433/29; 433/215
(58) Field of Classification Search ................... 433/29, 433/215

See application file for complete search history.

(56) References Cited

U.S. PATENT DOCUMENTS

| | | | |
|---|---|---|---|
| 4,661,070 A | 4/1987 | Friedman | |
| 4,983,381 A * | 1/1991 | Torres Zaragoza | ............. 424/53 |
| 5,055,048 A | 10/1991 | Vassiliadis et al. | |
| 5,232,367 A | 8/1993 | Vassiliadis et al. | |
| 5,433,956 A | 7/1995 | Patel | |
| 5,645,428 A | 7/1997 | Yarborough | |
| 5,713,738 A | 2/1998 | Yarborough | |
| 6,106,293 A | 8/2000 | Wiesel | |
| 6,149,895 A | 11/2000 | Kutsch | |
| 6,231,343 B1 | 5/2001 | Ishibashi et al. | |
| 6,254,388 B1 | 7/2001 | Yarborough | |
| 6,361,320 B2 | 3/2002 | Yarborough | |
| 7,201,578 B2 * | 4/2007 | Yarborough | .................. 433/215 |
| 2006/0275016 A1 | 12/2006 | Boutoussov et al. | |
| 2007/0207442 A1 | 9/2007 | Yarborough | |

FOREIGN PATENT DOCUMENTS

| | | |
|---|---|---|
| JP | 2001/335450 A | 12/2001 |
| WO | 97/21420 A | 6/1997 |
| WO | 01/26577 A1 | 4/2001 |
| WO | 2008/019869 A1 | 2/2008 |
| WO | 2008/019870 A1 | 2/2008 |

* cited by examiner

*Primary Examiner* — John J Wilson
(74) *Attorney, Agent, or Firm* — Gudrun E. Huckett

(57) ABSTRACT

In a method for operating a laser system for bleaching teeth, a water-containing bleaching agent applied onto teeth is heated by a laser beam, wherein the laser beam has a wavelength in a range of 2.6 µm, inclusive, to 3.1 µm, inclusive, or in a range of 9.0 µm, inclusive, to 11.0 µm, inclusive. The laser system is operated in pulse mode with individual pulses of the laser beam, wherein the individual pulses each have a fluence that is below a vaporization threshold fluence of the bleaching agent.

22 Claims, 4 Drawing Sheets

METHOD FOR OPERATING A LASER SYSTEM FOR BLEACHING TEETH

BACKGROUND OF THE INVENTION

The invention relates to a method for operating a laser system and to a laser system for bleaching teeth.

White teeth have long been considered cosmetically desirable. For this reason, methods have been introduced to whiten teeth that are naturally off-white or have become stained by smoking or food intake. Teeth whitening can be achieved in two ways: firstly, with gels, pastes or liquids including toothpastes that are mechanically agitated at the stained tooth surface in order to effect tooth stain removal through abrasive erosion of the stained acquired pellicle; and, secondly, with gels, pastes or liquids that accomplish the tooth bleaching effect by a chemical process while in contact with the stained tooth surface for a specified period of time, after which the formulation is removed. The present invention pertains to chemical strategies for removing or destroying tooth stains by means of aqueous gels or pastes.

Bleaching gels typically consist of water and at least one bleaching agent selected from the group consisting of hydrogen peroxide and compounds that release hydrogen peroxide ($H_2O_2$) in water. In addition, gels contain also some or all of the following compounds: a thickening agent (for example, polyacrylic acid); a stabilizing agent (for example, amino carboxylic acid/salt); and a neutralizing agent that serves to neutralize the thickening agent. The gels are used in that the aqueous gel is applied to the teeth and removed after a certain residence time. Water is the principal component of the aqueous gel and is preferably present in an amount of more than 50% by weight. The bleaching agent is present in an amount ranging from 3% to 50%, most preferably 35%, by weight of the aqueous gel. Higher amounts of bleaching agent are preferred so that the gel may serve as a "fast acting bleaching gel" capable of bleaching teeth with only one or two applications. The right combination of thickening agent and stabilizing agent provides a gel that can be loaded with hydrogen peroxide and remains sufficiently stable to provide a suitable gel in regard to viscosity considerations and with little hydrogen peroxide decomposition after four to twelve weeks storage at room temperature and even longer periods of time when refrigerated.

In a typical treatment process, the dental bleaching gel is brought into contact with the teeth that are to be bleached. The dental bleach is then allowed to remain in contact with the teeth for a residence time ranging anywhere from 5 minutes to one hour. The degree of whitening provided by the gel increases with time of contact between the reactive species of peroxide and the tooth enamel surface, and the rate of activation of the gel in terms of generating available peroxide ($H_2O_2$) and/or its reactive species (OH and O). Due to its chemical structure, the peroxide must produce transient species, such as OH and O, before the final products, $H_2O$ and $O_2$ are generated by the following mechanism:

The presence of the active transient species (radical OH and atomic oxygen O) plays the most important role in the whitening process due to the high reactivity of the transient species.

The bleaching effect is directly proportional to the residence time. However, the bleaching effect can be amplified by applying a heating element, a heat light, or a laser light to the dental bleaching gel once it is in place on the teeth. The heat and light serve to increase the rate of bleaching of the hydrogen peroxide, providing a shorter period of time in which whitening of the teeth is achieved. The increased effectiveness and speed of the whitening process at higher temperatures is due to the faster generation and mobility of $H_2O_2$ in the peroxide gel, the decomposition of $H_2O_2$ to OH and O, the enhanced diffusion rate into the tooth as well as the enhanced reaction time between the active peroxide species (which can be radicals of OH or atomic oxygen O) and the compounds of the enamel and dentin. Typical temperature increases that are desirable in such procedures are between 10° C. and 30° C.

When laser light is used for the amplification of the bleaching effect, typically a plurality of discrete laser enhancing particles are added to the gel. The particles are capable of absorbing the light energy from the wavelength of light emitted from the laser and of re-transmitting the light energy as thermal energy. These particles are dispersed throughout the bleaching compositions so that the laser beam can pass through the surface of the tooth while the particles absorb a portion of the light energy from the laser and retransmit it as thermal energy thus increasing the effectiveness of the bleaching composition. For example, an argon laser utilizes a blue light with a wavelength in the range of 470 nm to 520 nm. The complementary color to blue is orange, and thus an orange or red-colored or pigmented particulate material that absorbs in this range would be suitable. Also preferred are other colors that absorb at the wavelength of the utilized laser light. For example, a black particulate material absorbs across all wavelengths and would thus also be suitable. Other typically used lasers for heat enhanced teeth whitening are diode lasers with a wavelength of 810 nm or Nd:YAG lasers with a wavelength of 1,064 nm.

Some of the disadvantages of the existing laser light enhancing methods will be explained in the following. A special bleaching gel that contains additional laser light absorbing particles must be used. A special laser device that emits at the absorbing wavelength of the enhancing particles must be used. Special care must be taken that the laser enhancing particles are non-poisonous and biocompatible. It may be difficult to clean the teeth colored by the laser enhancing particles after the procedure. The density of the added absorbing particles is typically such that the laser light is not fully absorbed in the relatively thin layer of the gel that is deposited on the tooth surface. As a result, the laser is transmitted to the tooth surface and possibly transmitted into the dental tissue. This can result in an undesirable heating of the hard dental tissue and of the dental pulp, possibly leading to pain and irreversible damage. Indeed, some of the treatment procedures recommend applying laser light to a tooth for a duration within a certain range until the patient reports feeling pain.

In a completely different scenario, far infrared lasers are used for ablative applications in dentistry. At certain wavelengths of the laser a high absorption in water is encountered causing heating and vaporization of the water. Since human tissue contains at least some water, the laser energy absorption in water is used for causing sudden vaporization similar to micro-explosions which leads to tissue ablation. However, such far infrared laser heating has not been proposed for teeth whitening for numerous reasons.

Firstly, there is a significant safety concern. As water is an important component of hard dental tissues, enamel and dentin as well, these wavelengths are therefore highly absorbed in the enamel and dentin, and for this reason are used in hard tissue treatments, such as cavity preparations or enamel etching. There is therefore a danger that unnecessary damage to the enamel might occur when the radiation from these lasers is accidentally directed to an unprotected area of the tooth during a teeth whitening procedure.

Secondly, there is also an efficacy concern. Because of the extremely high absorption in water, these laser wavelengths are absorbed in a very shallow, only approximately three micron deep, surface layer of the aqueous bleaching gel. As a result, the surface of the bleaching gel can become very hot and can even be vaporized while the deeper layers of the gel are not affected and not heated by the laser light. These problems are particularly pronounced due to the fact that most of the known far infrared dental ablative lasers operate effectively only in a pulsed mode with relatively short laser pulses and relatively high laser pulse power. Far infrared ablative lasers have therefore not been proposed for use in teeth whitening.

SUMMARY OF THE INVENTION

The present invention has the object to provide a method for operating a laser system for bleaching teeth at high efficacy.

This object is solved by a method according to the invention wherein a water-containing bleaching agent applied onto the teeth is heated by means of a laser beam, wherein the laser beam has a wavelength in a range of 2.6 µm, inclusive, to 3.1 µm, inclusive, or in a range of 9.0 µm, inclusive, to 11.0 µm, inclusive, wherein the laser system is operated in pulse mode with individual pulses of the laser beam and wherein the individual pulses each have a fluence that is below a vaporization threshold fluence of the bleaching agent.

The present invention further has the object to provide a laser system for bleaching teeth at high efficacy.

This object is solved by a laser system generating a laser beam, wherein the laser beam has a wavelength in a range of 2.6 µm, inclusive, to 3.1 µm, inclusive, or in a range of 9.0 µm, inclusive, to 11.0 µm, inclusive, wherein the laser system is adapted to be operated by the method according to the present invention for bleaching teeth in cosmetic or non-cosmetic applications.

A method and a laser system are proposed according to which a water-containing bleaching agent applied to the teeth is heated by means of a laser beam wherein the laser beam has a wavelength in a range of 2.6 µm, inclusive, to 3.1 µm, inclusive, or in a range of 9.0 µm, inclusive, to 11.0 µm, inclusive, wherein the laser beam is operated in pulse mode with individual pulses and wherein the individual pulses each having a fluence that is below the vaporization threshold fluence of the bleaching agent.

In an advantageous embodiment, the wavelength of the laser beam and the water-containing bleaching agent together provide a characteristic pulse time. The pulse duration of the individual pulses is selected to be greater than the characteristic pulse time. Preferably, it is at least twice as great, and particularly at least three times as great, as the characteristic pulse time.

The present invention offers solutions to the problems described above which are related to the use of laser sources for heat activation of a teeth whitening process.

The invention makes use of the fact that the above specified wavelength of the pulsed far infrared laser beam is at or close to water absorption peaks in the vicinity of 3 µm and 10 µm. With the further specified pulses and fluence, the inventive procedure can be safely and efficiently used for heat activation of teeth whitening.

The inventive selection of a laser wavelength that is absorbed in the major component of the aqueous bleaching gel, i.e., in water, eliminates the need for any additional absorbing particles or any special bleaching gels. The laser parameters are adjusted for the bleaching treatments so that the laser fluence of every laser pulse is significantly below the vaporization threshold fluence for the bleaching gel and the ablation threshold fluence for the hard dental tissues. The bleaching gel will not be vaporized and there is no risk of damaging the hard dental tissue.

The heat is being transmitted by means of heat diffusion away from the heated surface layer to the deeper tissue layers. The characteristic depth $x_d$ to which the tissue temperature is affected by heat diffusion after a time t can be estimated as follows:

$$x_d = (D \cdot t)^{1/2}$$

wherein D is the thermal diffusivity of the irradiated material. For the bleaching gel and enamel, the thermal diffusivity is estimated to be $2 \times 10^{-7}$ m$^2$/s and $4 \times 10^{-7}$ m$^2$/s, respectively. From the above, we can estimate that the diffusion cannot be neglected when pulse durations are longer than the characteristic pulse time $\tau$ calculated as follows:

$$\tau = 1/(DC^2)$$

where C is the absorption coefficient of the laser light in the irradiated material. For the enamel this characteristic pulse time is approximately 100 µs, when an Er:YAG laser is used, and the absorption coefficient C in the enamel at the Er:YAG wavelength is taken to be 150 mm$^{-1}$. The absorption coefficient in the bleaching gel depends on the exact composition of the gel, and especially on the content (concentration) of water in the gel. Assuming the absorption coefficient of the Er:YAG wavelength in the bleaching gel of C=300 mm$^{-1}$ (representing a gel consisting of approximately 70% of water), the characteristic pulse time for the Er:YAG in this gel would be approximately 50 µs. And assuming the absorption coefficient C of the Er:YAG wavelength in the gel to be C=150 mm$^{-1}$, the corresponding pulse characteristic time is approximately 200 µs. Therefore, at pulse durations longer, and preferably significantly longer than the above characteristic times, the ablation thresholds will increase above the non-diffusion value due to the conductive loss of heat from the surface layer. This is beneficial for the bleaching process as the potential problem of gel vaporization and enamel etching can be excluded by extending the laser pulse duration significantly above the characteristic pulse time, i.e., at least twice the characteristic pulse time, and preferably at least three times the characteristic pulse time.

In order to achieve heating of the deeper lying bleaching gel layers, the laser energy is delivered in a sequence of laser pulses, each below the vaporization threshold fluence and enamel ablation threshold fluence at a repetition rate preferably in the range of 1 Hz to 100 Hz. This results in the accumulation of heat also in the deeper lying layers of the gel. The laser pulses, each below the vaporization threshold fluence, are separated by a time period preferably not shorter than ten times the characteristic pulse time, in order for the initial temperature distribution following each pulse to be wiped away by the heat diffusion before the next pulse arrives.

The individual pulses advantageously comprise an at least approximate rectangular course of power density over time. This ensures that no undesired significant peaks occur over the average value, and that the resulting temporal power density, in addition to the total pulse fluence, is always below threshold.

In an advantageous embodiment, the laser system comprises an Er:YAG laser whose laser beam has a wavelength of approximately 2.94 µm. The fluence of the individual pulses is expediently $\leq 0.1$ J/cm², respectively. The characteristic pulse time for the Er:YAG laser is approximately 50-200 µs. In this connection, the pulse duration of the individual pulses is selected to be in particular greater, and preferably significantly greater than these 50-200 µs. The absorption of the laser beam of the aforementioned wavelength in water is almost at maximum so that a high efficiency can be obtained with minimal power expenditure.

In an expedient alternative the laser system comprises an Er,Cr:YSGG laser whose laser beam has a wavelength of approximately 2.78 µm. The fluence of the individual pulses is selected to be advantageously $\leq 0.3$ J/cm², respectively. Since this wavelength has approximately three times smaller absorption coefficient in water when compared with Er:YAG, the characteristic pulse time for the Er,Cr:YSGG laser is approximately nine times longer in comparison to the characteristic pulse time for the Er:YAG, and lies in the range of 450-1800 µs. The pulse duration (t) of the individual pulses is in particular greater, and preferably significantly greater than these 450-1800 µs.

In another preferred alternative, the laser system comprises a $CO_2$ laser whose laser beam has a wavelength of approximately 10.6 µm. The fluence of the individual pulses is selected to be expediently $\leq 1.0$ J/cm². Since this wavelength has approximately ten times smaller absorption coefficient in water when compared with the Er:YAG, the characteristic pulse time for the CO2 laser is approximately hundred times longer in comparison to the characteristic pulse time for the Er:YAG, and lies in the range of 5,000-20,000 µs (5-20 ms). The pulse duration (t) of the individual pulses is selected to be in particular greater, and preferably significantly greater than these 5,000-20,000 µs.

The Er,Cr:YSGG laser (2.78 µm) has a 3 times lower absorption in the 3 µm range. In the 10 µm range, the $CO_2$ laser with the 10.6 µm wavelength is available with approximately 10 times lower absorption compared to the Er:YAG laser. Nevertheless, the absorption of both lasers is sufficient to achieve an efficient teeth bleaching.

Overall, an efficient heating of the bleaching gel and thus an efficient teeth whitening is created thus overcoming the prior art drawbacks.

An additional advantage would be that these lasers could also be used for the ablation of hard and soft dental tissues, as such tissues contain also a significant amount of water. In particular, Er:YAG lasers and Er,Cr:YSGG lasers are becoming standard laser tools in many dental practices for treating hard and soft dental tissues. The ablation of hard dental tissue results from micro-explosions caused by vaporized tissue water where such radiation is predominantly absorbed. Adding another application for use (i.e., teeth whitening) for these lasers would be beneficial to dentists as they would not have to acquire an additional special laser only for teeth whitening.

In an advantageous embodiment, the individual pulses are selected to each have a fluence that is below the ablation threshold fluence of the dental tissue. The measured Er:YAG ablation threshold fluences in enamel are approximately 1.5 J/cm² for $t_p$=80 µs, 3.1 J/cm² for $t_p$=250 µs, and 6.8 J/cm² for $t_p$=800 µs, all safely above the fluence of 0.1 J/cm². Similarly, the measured Er,Cr:YSGG ablation threshold fluences in enamel are approximately 4.2 J/cm² for $t_p$=500 µs, and 9.5 J/cm² for $t_p$=1,300 µs, all safely above the fluence of 0.3 J/cm².

In an advantageous embodiment, a required average power density (in W/cm²) of the sequence of the individual pulses is adjusted for heating the bleaching agent such that a total irradiation time of $\leq 30$ seconds results. Here, the average power density is defined as the single pulse fluence (in J/cm²) divided by the temporal spacing $\Delta t$ between the pulses (in s).

The temperature increase of the bleaching gel changes with different average laser power densities (different repetition rates of a constant single pulse energy) for the same cumulative fluence of all the pulses in the sequence. The time required to deliver the same cumulative fluence decreases with the average power density. At lower power densities, and correspondingly longer irradiation times, the final gel temperature increase is lower. This is attributed to cooling as a result of loss of energy into the tooth and into the surrounding (ambient temperature). Optimal irradiation times are therefore at or below 30 seconds.

Similar experiments with a diode (810 nm) or an Nd:YAG (1,064 nm) laser (that are typically used for heat enhanced teeth whitening in the prior art) show that, in order to achieve the same temperature increase of the bleaching gel as with an Er:YAG laser, much larger cumulative fluences are required. For example, in order to achieve a temperature increase of 30° C. in a time period of 30 seconds, an average power density of approximately 18 W/cm² must be applied resulting in a delivered cumulative fluence of 540 J/cm² which is more than ten times higher compared to the treatment with an Er:YAG laser. This is due to the fact that these laser wavelengths are not fully absorbed in the bleaching gel but are transmitted into the tooth. Therefore, energy is being wasted for undesirable and potentially painful and/or damaging heating of the tooth itself.

In a preferred embodiment, a hand piece for guiding the laser beam to the bleaching agent is provided wherein the laser beam is collimated and, in particular, exits from the hand piece at a diameter in a range of 2.0 mm, inclusive, to 10.0 mm, inclusive. Preferably, the laser beam exiting from the hand piece has at least approximately a top hat profile. The collimated, i.e., parallel orientated, course of the rays of the exiting laser beam has the result that the spacing of the hand piece to the tooth surface or to the applied bleaching agent is not critical for the treatment. The surface area that is illuminated by the laser beam on the bleaching agent is independent of the spacing. Without requiring spacer means or other auxiliary means, the person carrying out the treatment can guide the hand piece freely to the treatment site and can ensure a uniform treatment intensity. The indicated diameter range enables a targeted heating of the bleaching agent without unnecessarily heating surrounding areas outside of the desired target area. The top hat profile of the exiting laser beam leads to a uniformly distributed illumination intensity across the treatment surface. A uniform heating of the bleaching agent without temperature peaks is achieved. A particular feature of the present method resides in that the laser source, in contrast to the ablative method, is operated at low laser pulse fluence and simultaneously at comparatively long pulse duration; this is required for a fluence below the vaporization threshold. This can lead to the laser operation becoming instable if no additional measures are provided. In order to prevent instable operation, in an advantageous embodiment means for reducing the laser energy impinging on the bleaching agent are provided, in particular in the form of a beam splitter or an adsorption filter. In this connection, the laser can be operated at a power providing a stable state which power is above the demand required for heating the bleaching agent. The excess energy not required for heating the bleaching agent is branched off by means of the beam splitter, the absorption filter or other suitable means for reducing the laser energy of the laser beam impinging on the bleaching agent.

The remaining laser energy that is guided by the hand piece to the bleaching agent and impinges on the bleaching agent has the required minimal level.

DESCRIPTION OF PREFERRED EMBODIMENTS

Figure 1:
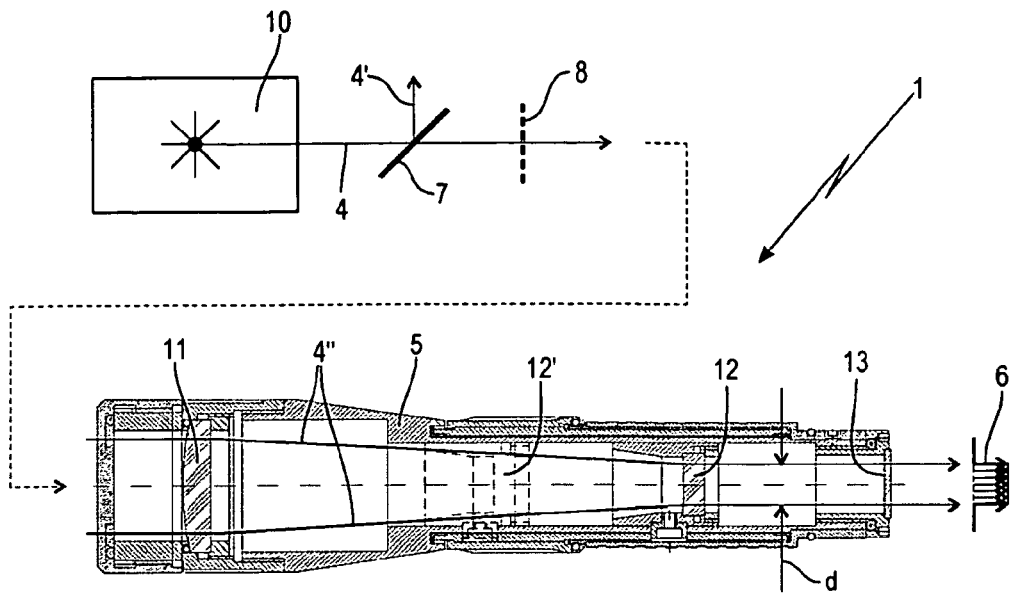
FIG. 1 shows in a schematic, partially sectioned illustration, a laser system with a hand piece for performing the method according to the invention wherein the course of the beam is illustrated as well.

FIG. 1 shows in a schematic, partially sectioned illustration a laser system 1 with a laser source 10 and a hand piece 5 for performing the method according to the invention. This method is a method for cosmetic bleaching of teeth 2 illustrated schematically in FIGS. 8 and 9 and a method for operating a laser system 1 for the cosmetic bleaching of teeth 2.

The laser source 10 generates a laser beam 4 that is guided by means (not illustrated), for example, an articulated arm or a fiber, to the hand piece 5 connected to the end. The hand piece 5 can be freely guided by the user to the treatment site wherein the laser beam 4 passes through the hand piece 5. The laser beam 4 passing through the hand piece 5 is limited by outer boundary rays 4". The boundary rays 4" illustrate that the laser beam 4 entering with a comparatively large diameter is collimated, i.e., is orientated in parallel. First, it passes through a plane-convex lens 11 that causes the diameter of the beam passing through it to taper conically. Subsequently, the laser beam 4 passes through a plane-concave lens 12 that, with regard to its optical properties, is designed such that the laser beam 4 as it exits and as it enters the hand piece 5 is collimated. Subsequently, the laser beam 4 passes through a plane-parallel window 13 to the treatment port. The exit window 13 made of transparent material as glass or the like has no additional optical properties and serves only as a protective means of the hand piece 5 and of the optical system arranged therein.

The laser beam 4 exiting from the plane-concave lens 12 has a diameter d that is reduced in comparison to that of the incoming laser beam 4. The diameter d is preferably in a range of 2.0 mm, inclusive, to 10.0 mm, inclusive, and can be fixedly preset by constructive measures. In the illustrated embodiment, the plane-concave lens 12 can be moved back and forth between the illustrated position remote from the plane-concave lens 11 and a position closer thereto and identified by 12' so that the diameter d of the exiting laser beam 4 can be adjusted within the aforementioned value range. Independent of the positioning of the plane-concave lens 12, the exiting collimated laser beam 4 has a top hat profile 6. This means that a circular disk-shaped illumination with a uniformly distributed laser energy across the illuminated surface area is provided. However, larger beam diameters may be desirable. In addition, it would be advantageous to form instead of a circular beam cross section an elongated beam cross section, which could be elliptical or in other way elongate, in order to treat more than one tooth at the same time.

Inasmuch as the laser energy of the laser beam 4 exiting from the laser source 10 is too high for the method according to the invention, in the path of the laser beam 4 a beam splitter 7, an absorption filter 8 or a combination of both can be arranged optionally. By means of the beam splitter 7 a partial beam 4' of the laser beam 4 is branched off. The absorption filter 8 absorbs a portion of the laser energy passing through it. In both cases, only a residual, reduced energy quantity reaches the treatment site which energy quantity has been lowered to the required level for the inventive method by a suitable configuration of the beam splitter 7, the absorption filter 8 or the other suitable means.

The laser beam 4 according to FIG. 1 has a wavelength $\lambda$ as a function of which the laser beam 4 experiences absorption in water which absorption is defined by the absorption coefficient C. The curve of the absorption coefficient C as a function of the wavelength $\lambda$ is illustrated in a partially enlarged diagram illustration in FIG. 2. It can be seen that this curve in the area of a wavelength $\lambda$ of approximately 3 μm and approximately 10 μm has a peak, respectively. In these peaks, the absorption of the laser beam 4 (FIG. 1) in water is comparatively high, i.e, leads to comparatively high heating of the water, even for minimal energy introduction.

Figure 2:
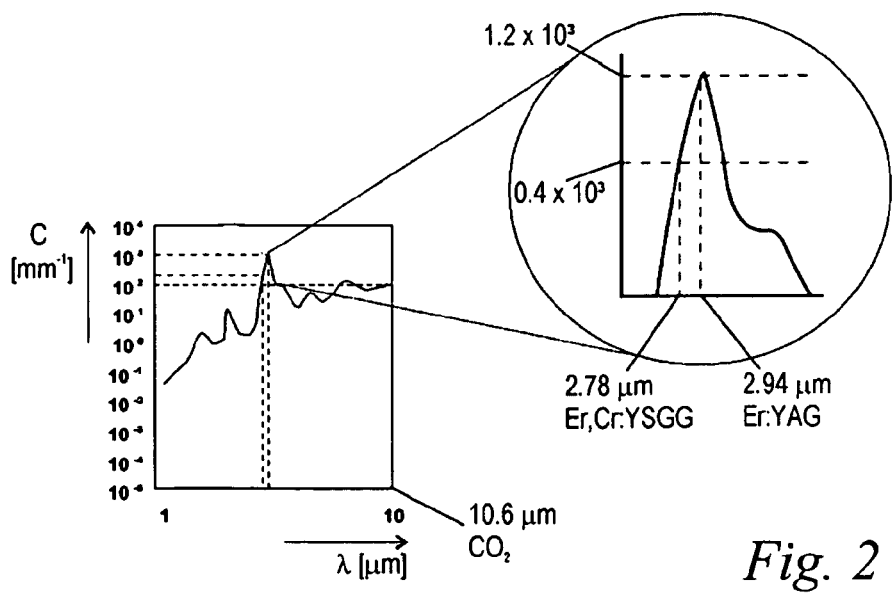
FIG. 2 shows in a partially enlarged diagram illustration the curve of the laser absorption in water as a function of the wavelength.

By referring at the same time to FIGS. 1 and 2, a laser source 10 is selected from a group whose laser beam 4 has a wavelength $\lambda$ in a range of 2.6 μm, inclusive, to 3.1 μm, inclusive, or in a range of 9.0 μm, inclusive, to 11.0 μm, inclusive, i.e., it is within the far infrared range, and covering the a.m. peaks with a high absorption coefficient C. In particular, the laser source 10 is either an Er:YAG laser with a wavelength $\lambda$ of approximately 2.94 μm, an Er,Cr:YSGG laser with a wavelength of 2.78 μm, or a $CO_2$ laser having a wavelength of approximately 10.6 μm. The illustration of FIG. 2 shows that the absorption coefficient C for the Er:YAG laser is approximately $1.2 \times 10^3$ $mm^{-1}$, for the Er,Cr:YSGG laser approximately $0.4 \times 10^3$ $mm^{-1}$, and for the $CO_2$ laser approximately $1.2 \times 10^2$ $mm^{-1}$. The absorption coefficient C of the Er,Cr:YSGG laser is only about one-third of the absorption coefficient C of the Er:YAG laser, and that of the $CO_2$ laser is only approximately 1/10 of the absorption coefficient C of the Er:YAG laser. The surface heating effect of the laser beam 4 in water is thus greatest for the Er:YAG laser.

Figure 3:
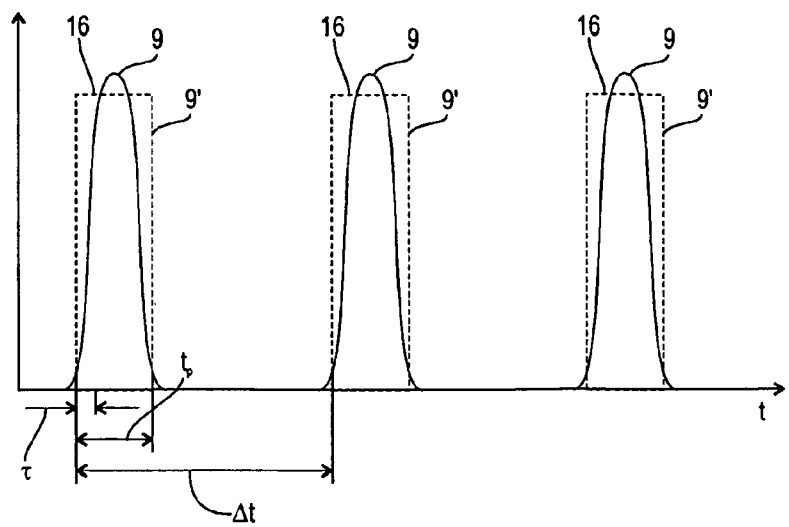
FIG. 3 is a schematic diagram illustration of the pulse power density curve in accordance with the present invention plotted against time.

In all cases, the laser system 1 is operated in pulse mode with individual pulses 9 of the laser beam 4 wherein the temporal power density course of the pulse 9 is illustrated schematically in FIG. 3. According to FIG. 3 the pulses 9 may have a curved course over time t. However, it would be advantageous to provide an at least approximate rectangular course over time t, as depicted at 9', comprising a flat top 16 as maximum value. This ensures that no undesired significant peaks occur over the average value, and that the resulting pulse fluence F is always below threshold fluence $F_{th}$, being illustrated diagrammatically in FIGS. 4, 5, and 6, and described in detail below.

The individual pulses 9 have each a pulse duration $t_p$ as well as a temporal spacing Δt relative to one another. Moreover, based on the wavelength λ of the employed laser beam 4 (FIGS. 1 and 2), respectively, and of the material properties of the water-containing bleaching agent 3 (FIGS. 8 and 9), a characteristic pulse time τ will result. The pulse duration $t_p$ of the individual pulses 9 is greater than the characteristic pulse time τ and is preferably at least twice as large and in particular at least three times as large as the latter. In the illustrated embodiment, it is approximately 3.5 times as large. For the Er:YAG laser, the characteristic pulse time τ is in a range of 50 μs, inclusive, to 200 μs, inclusive, for the Er,Cr:YSGG laser it is in a range of 450 μs, inclusive, to 1800 μs, and for the $CO_2$ laser it is in a range of 5000 μs (=5.0 ms), inclusive, to 20000 μs (=20.0 ms), wherein the respective pulse duration $t_p$ in accordance with the above condition is correspondingly greater. The temporal spacing Δt between the individual pulses 9 is selected such that they follow one another at a frequency which is within the range of 1.0 Hz, inclusive, to 100 Hz, inclusive. In this connection, the temporal spacing Δt between the individual pulses 9 is at least as large as ten times the characteristic pulse time τ.

Figure 4:
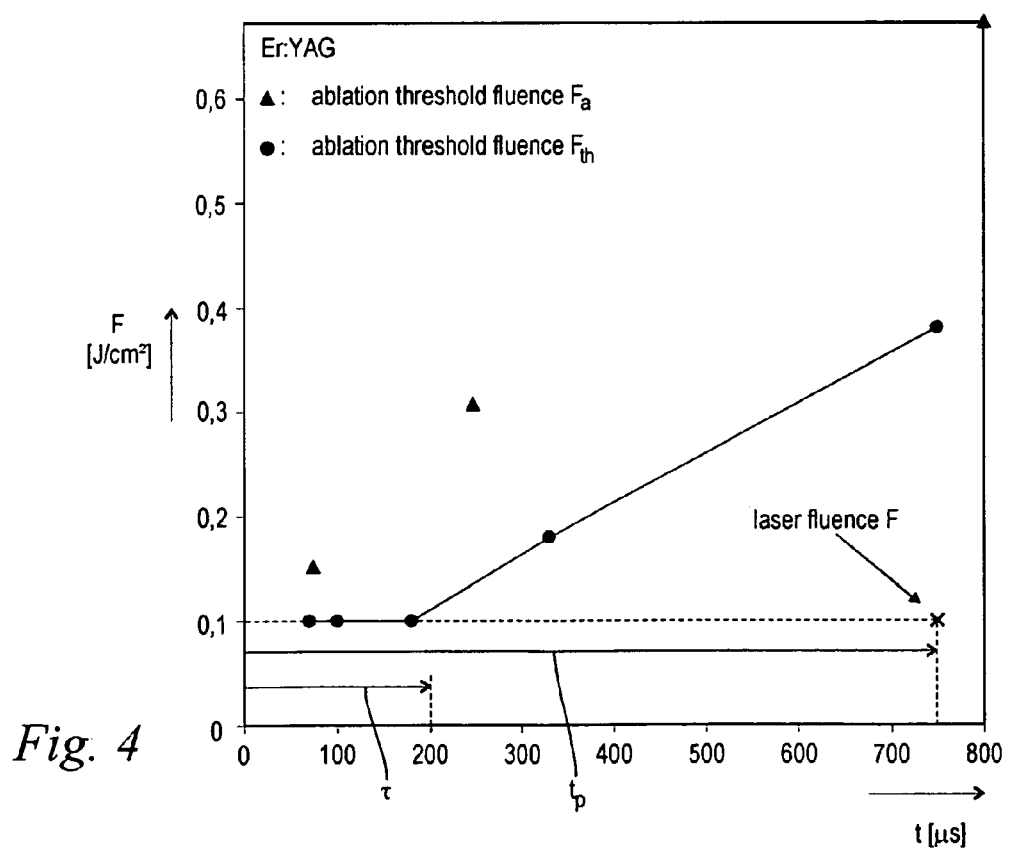
FIG. 4 shows a diagram illustration of the selected laser fluence in operation of an Er:YAG laser in comparison to the curve of the vaporization threshold plotted against the pulse duration.
Figure 5:
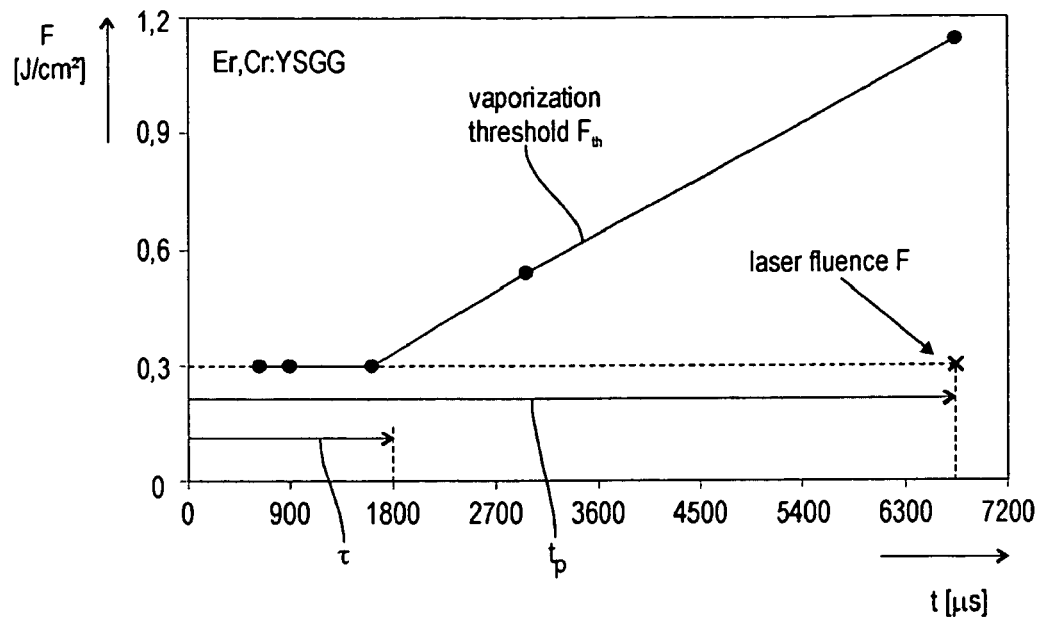
FIG. 5 shows a further diagram illustration of the selected laser fluence in connection with the operation of an Er,Cr:YSGG laser in comparison to the curve of the vaporization threshold plotted against the pulse duration.
Figure 6:
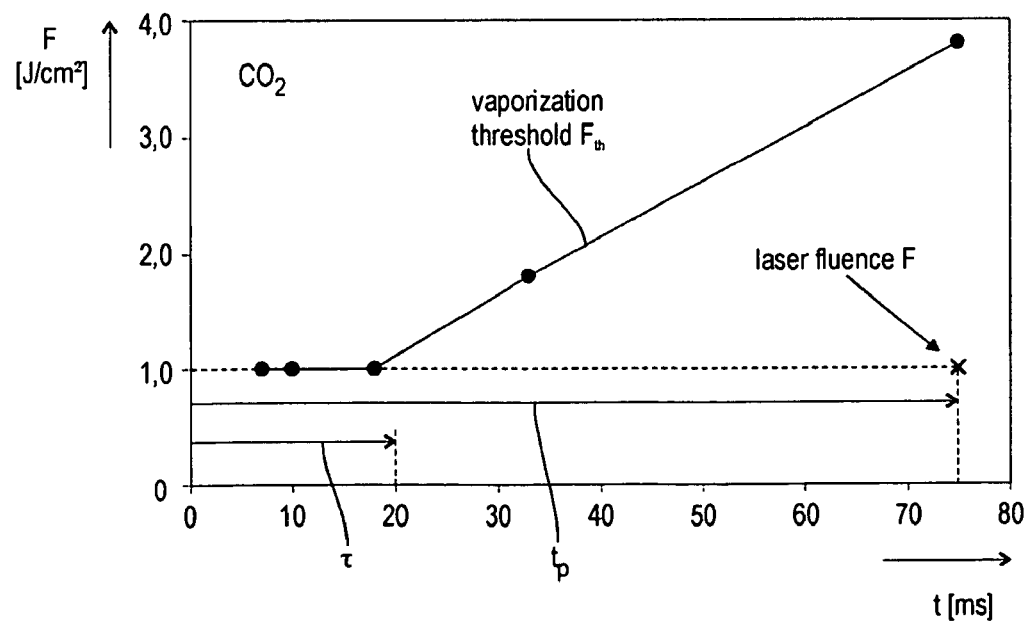
FIG. 6 is a further diagram illustration of the selected laser fluence in connection with the operation of a $CO_2$ laser in comparison to the curve of the vaporization threshold plotted against the pulse duration.

The individual pulses 9 according to FIG. 3 have a fluence F below a vaporization threshold fluence $F_{th}$ of the bleaching agent 3, and below an ablation threshold fluence $F_a$ of the dental tissue of the teeth 2, that is illustrated diagrammatically in FIGS. 4, 5, and 6 for different laser sources 10 (FIG. 1). The water-containing bleaching agent 3 (FIGS. 8 and 9) has under the effect of the fluence F a vaporization threshold $F_{th}$ whose curve as a function of the pulse duration $t_p$ is also illustrated in FIGS. 4, 5, and 6. FIG. 4 shows in this connection the relationships for the Er:YAG laser while the relationships for the Er,Cr:YSGG laser is shown in FIG. 5 and those for the $CO_2$ laser is shown in FIG. 6. In all three cases it can be seen that the vaporization threshold fluence $F_{th}$ is approximately constant below the characteristic pulse time T and is approximately 0.1 $J/cm^2$ for the Er:YAG laser; approximately 0.3 $J/cm^2$ for the Er,Cr:YSGG laser, and approximately 1.0 $J/cm^2$ for the $CO_2$ laser. Above the characteristic pulse time τ, the vaporization threshold fluence $F_{th}$ increases approximately linearly, respectively.

Figures 8, 9:
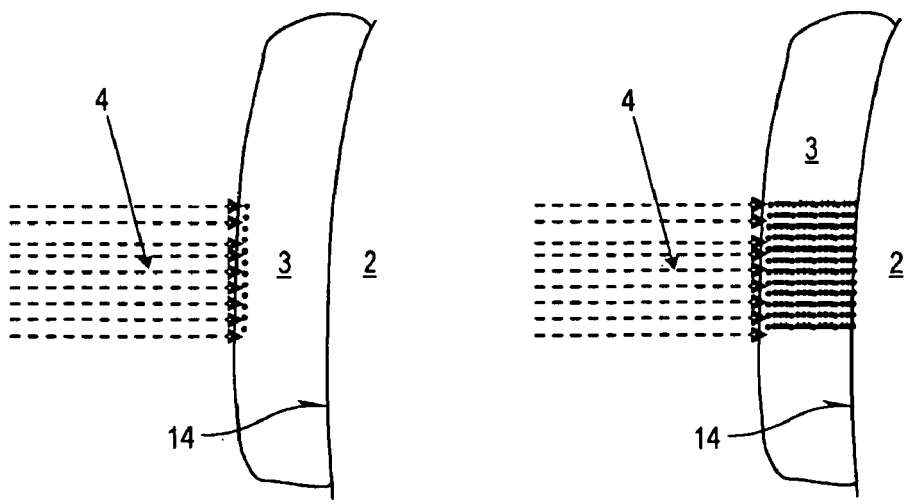
FIG. 8 shows a schematic side view of the tooth surface with applied bleaching agent at the beginning of the action of the laser beam.
FIG. 9 shows the arrangement according to FIG. 8 after extended irradiation time of the laser beam with uniformly heated bleaching agent.

When looking at FIGS. 3 through 6, the individual pulses 9 each have a fluence F that is significantly below the vaporization threshold fluence $F_{th}$ of the bleaching agent 3 (FIGS. 8, 9). For this purpose,-for the Er:YAG laser (FIG. 4) a fluence F of approximately 0.1 $J/cm^2$ at a pulse duration $t_p$ of approximately 750 μs is selected, as illustrated by x. Accordingly, the illustrated pulse duration $t_p$ shown as an example is approximately 3.5 times the characteristic pulse time τ while the corresponding fluence F is approximately only one-fourth of the vaporization threshold fluence $F_{th}$ indicated a this location at 0.4 $J/cm^2$. At the same time, the fluence F is approximately as large as the vaporization threshold fluence $F_{th}$ in the range of the characteristic pulse time τ but, for the purpose of providing a safety spacing relative to the vaporization threshold, can also be selected to be smaller. Alternatively, greater values of the fluence F and/or smaller values of the pulse duration $t_p$ are possible as long as this provides a value pair that is located with sufficient safety spacing below the correlated vaporization threshold fluence $F_{th}$. The same holds true essentially also for the Er,Cr:YSGG laser according to FIG. 5 and for the $CO_2$ laser according to FIG. 6. The vaporization threshold fluence $F_{th}$ increases starting at 0.3 $J/cm^2$ or 1.0 $J/cm^2$ above the respective characteristic pulse time τ of 1800 μs or 20000 μs (=20 ms). The correlated value pairs of the pulses 9 are 0.3 $J/cm^2$ at 6750 μs or 1.0 $J/cm^2$ at 75 ms. The above remarks in connection with Er:YAG apply also with regard to the advantageous possible value ranges.

It is further shown in FIG. 4, that the measured Er:YAG ablation threshold fluences $F_a$ in enamel are approximately 1.5 $J/cm^2$ for $t_p$=80 μs, 3.1 $J/cm^2$ for $t_p$=250 μs, and 6.8 $J/cm^2$ for $t_p$=800 μs, all safely above the laser fluence F of 0.1 $J/cm^2$. Similarly, the measured Er,Cr:YSGG ablation threshold fluences in enamel are approximately 4.2 $J/cm^2$ for $t_p$=500 μs, and 9.5 $J/cm^2$ for $t_p$=1300 μs, all safely above the fluence of 0.3 $J/cm^2$. The measured Er,Cr:YSGG ablation threshold fluences are not shown in FIG. 5 for clarity reasons.

Figure 7:
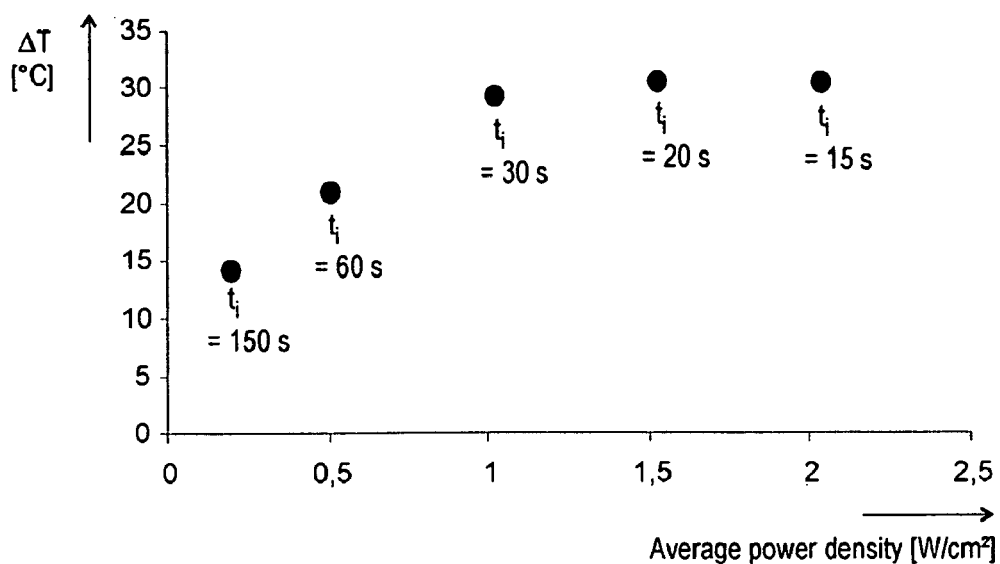
FIG. 7 is a diagram illustration of the temperature increase obtainable in the bleaching agent as a function of the average power density for different laser irradiation times.

FIG. 7 shows a diagram illustration of the temperature increase ΔT achieved in the bleaching agent 3 (FIGS. 8, 9) by irradiating the bleaching agent with the laser beam 4 with the cumulative fluence of 30 $J/cm^2$. Five values for five different average power densities are shown. For constant individual pulse fluence but different pulse frequencies or temporal spacings Δt between the individual pulses 9 (FIG. 3), the same cumulative fluence is introduced into the bleaching agent 3 at different total irradiation times $t_i$. For example, five different average power densities shown in FIG. 7 require for the same cumulative fluence of 30 $J/cm^2$ five different total irradiation times $t_i$ of 150 seconds, 60 seconds, 30 seconds, 20 seconds, and 15 seconds. As can be seen, at low average power densities, and therefore long irradiation times $t_i$, the temperature increase ΔT is lower compared to the situation when higher average power densities in correspondingly shorter irradiation times are applied. For example, a comparatively minimal temperature increase ΔT of approximately 14° C. is reached at 150 seconds with a power density of 0.2 $W/cm^2$ and approximately 22° C. at 60 seconds with a power density of 0.5 $W/cm^2$. This is caused by energy loss as a result of heat dissipation into the tooth 2 (FIG. 8, FIG. 9) and into the surroundings during the irradiation time. The loss due to heat dissipation is smaller at shorter irradiation times. However, as can be seen from FIG. 7, by decreasing the irradiation times below 30 s the temperature increase ΔT does not improve appreciably. The time of 30 s thus represents an approximate heat dissipation time of the tooth. Accordingly, the aforedescribed parameters of the method are adjusted preferably such that an total irradiation time $t_i$ of ≦30 seconds results.

FIG. 8 shows a schematic side view of a tooth 2 at the beginning of the bleaching process according to the invention. On a surface 14 of the tooth 2 a water-containing bleaching agent 3 is applied which is in the form of a gel and in this way adheres in the required thickness on the surface 14 of the tooth 2. Instead of a gel, other water-containing formulations can be expedient. The water contents of the bleaching agent 3 is advantageously at least 50% by weight. In addition to thickening and stabilizing agents, a neutralizing agent for the thickening agent is also provided. Moreover, the bleaching agent 3 contains an active bleaching ingredient with a proportion between 3% by weight and 50% by weight, advantageously 35% by weight. The bleaching agent 3 serves for chemical bleaching of the discolored surface 14 of the tooth 2 wherein, for accelerating the bleaching effect, a temperature increase ΔT (FIG. 7) is generated by the impinging laser beam 4. The afore described parameters of the inventive methods have the result that at the beginning of the action time of the laser beam 4 first only the external surface of the bleaching agent 3 is heated (FIG. 8). With progressing action duration, the heat penetrates according to the illustration of FIG. 9 through the entire layer thickness of the bleaching agent 3 to the surface 14 of the tooth 2 without causing evaporation of the water-containing bleaching agent 3 or damage or overheating of the tooth 2. The uniform temperature increase ΔT achieved throughout the entire layer thickness of the bleaching agent 3 leads to a significant acceleration of the bleaching process without undesirable side effects. The specification incorporates by reference the entire disclosure of European priority documents 07 017 169.9 having a filing date of 1 Sep. 2007 and 08 014 107.0 having a filing date of 7 Aug. 2008.

While specific embodiments of the invention have been shown and described in detail to illustrate the inventive principles, it will be understood that the invention may be embodied otherwise without departing from such principles.

What is claimed is:

1. A method for operating a laser system for bleaching teeth, the method comprising the steps of:
   heating by a laser beam a water-containing bleaching agent applied onto teeth, wherein the laser beam has a wavelength in a range of 2.6 μm, inclusive, to 3.1 μm, inclusive, or in a range of 9.0 μm, inclusive, to 11.0 μm, inclusive;
   operating the laser system in pulse mode with individual pulses of the laser beam, wherein the individual pulses each have a fluence that is below a vaporization threshold fluence of the bleaching agent.

2. The method according to claim 1, wherein the wavelength of the laser beam and the water-containing bleaching agent together provide a characteristic pulse time, further comprising the step of selecting a pulse duration of the individual pulses to be greater than the characteristic pulse time.

3. The method according to claim 2, wherein the pulse duration of the individual pulses is selected to be at least twice as great as the characteristic pulse time.

4. The method according to claim 2, wherein the pulse duration of the individual pulses is selected to be at least three times as great as the characteristic pulse time.

5. The method according to claim 2, wherein the laser system comprises an Er:YAG laser whose laser beam has a wavelength of approximately 2.94 μm.

6. The method according to claim 5, further comprising the step of selecting the fluence of the individual pulses to be ≦0.1 J/cm$^2$, respectively.

7. The method according to claim 5, further comprising the step of selecting the characteristic pulse time to be in a range of 50 μs, inclusive, to 200 μs, inclusive, wherein the pulse duration of the individual pulses is selected to be greater than said characteristic pulse time.

8. The method according to claim 2, wherein the laser system comprises an Er,Cr:YSGG laser wherein the laser beam has a wavelength of approximately 2.78 μm.

9. The method according to claim 8, further comprising the step of selecting the fluence of the individual pulses to be ≦0.3 J/cm$^2$, respectively.

10. The method according to claim 8, further comprising the step of selecting the characteristic pulse time to be in a range of 450 μs, inclusive, to 1800 μs, wherein the pulse duration of the individual pulses is selected to be greater than said characteristic pulse time.

11. The method according to claim 2, wherein the laser system comprises a $CO_2$ laser wherein the laser beam has a wavelength of approximately 10.6 μm.

12. The method according to claim 11, further comprising the step of selecting the fluence of the individual pulses to be ≦1.0 J/cm$^2$, respectively.

13. The method according to claim 11, further comprising the step of selecting the characteristic pulse time to be in a range of 5,000 μs, inclusive, to approximately 20,000 μs, wherein the pulse duration of the individual pulses is selected to be greater than said characteristic pulse time.

14. The method according to claim 1, wherein the dental tissue of the teeth has an ablation threshold fluence, further comprising the step of selecting the individual pulses to each have a fluence that is below the ablation threshold fluence of the dental tissue.

15. The method according to claim 1, wherein the individual pulses comprise an at least approximate rectangular course of power density over time.

16. The method according to claim 1, further comprising the step of setting the individual pulses to follow one another at a frequency that is within a range of 1.0 Hz, inclusive, to 100 Hz, inclusive.

17. The method according to claim 1, wherein the wavelength of the laser beam and the water-containing bleaching agent together provide a characteristic pulse time, further comprising the step of providing a temporal spacing between the individual pulses that is at least as great as ten times the characteristic pulse time.

18. The method according to claim 1, further comprising the step of adjusting an average power density of a sequence of individual pulses required for heating the bleaching agent such that a total irradiation time ($t_i$) of ≦30 seconds results.

19. The method according to claim 1, wherein the laser system comprises a hand piece for guiding the laser beam to the bleaching agent, the method further comprising the step of collimating the laser beam and causing the laser beam to exit with a diameter in a range of 2.0 mm, inclusive, to 10.0 mm, inclusive, from the hand piece.

20. The method according to claim 19, wherein the laser beam exiting from the hand piece has at least approximately a top hat profile.

21. The method according to claim 1, further comprising the step of reducing the laser energy impinging on the bleaching agent.

22. The method according to claim 21, wherein in the step of reducing the laser energy a beam splitter or an absorption filter is used.

* * * * *